US006348140B1

(12) United States Patent
Matsubara et al.

(10) Patent No.: US 6,348,140 B1
(45) Date of Patent: Feb. 19, 2002

(54) GAS SENSOR WITH A HIGH COMBINED RESISTANCE TO LEAD WIRE RESISTANCE RATIO

(75) Inventors: Hideki Matsubara, Gifu; Noboru Matsui; Nobuhiro Hayakawa, both of Aichi, all of (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/541,903

(22) Filed: Apr. 3, 2000

(30) Foreign Application Priority Data

Apr. 1, 1999  (JP) .......................................... 11-095194

(51) Int. Cl.$^7$ ..................... G01N 27/407; G01N 27/409
(52) U.S. Cl. ..................... 204/424; 204/425; 204/426
(58) Field of Search .......................... 204/424, 425, 204/426; 73/23.32

(56) References Cited

U.S. PATENT DOCUMENTS 4,284,487 A  * 8/1981 Barnes et al. ............... 204/427
4,629,549 A  * 12/1986 Kojima et al. ............... 204/406
5,969,229 A  * 10/1999 Hori et al. .................. 73/23.31
6,071,393 A  * 6/2000 Oshima et al. .............. 204/425
6,120,663 A  * 9/2000 Kato et al. .................. 204/401

FOREIGN PATENT DOCUMENTS

EP             0 859 232 A2  * 8/1998

* cited by examiner

*Primary Examiner*—Robert J. Warden, Sr.
*Assistant Examiner*—Kaj K. Olsen
(74) *Attorney, Agent, or Firm*—Sughrue Mion, PLLC

(57) ABSTRACT

A high temperature sensor allowing for accurate measurement including wires running through an oxygen ion conductor and connecting to electrodes sandwiching an oxygen ion conductor substrate having an electrical resistance far smaller than the combined resistance (Rpvs) appearing across the lead wires, where Rpvs is determined by way of a pulse voltage sensing method applied across the electrodes. In the case of a two cavity sensor for NOx measurement, Rpvs is not less than 2.6 times greater, or more preferably 4 times greater than the resistance of the wires. In another embodiment, a common internal oxygen reference source cavity is formed inside the oxygen ion conductor so as to provide the same oxygen partial pressure base for other cavities.

14 Claims, 9 Drawing Sheets

GAS SENSOR WITH A HIGH COMBINED RESISTANCE TO LEAD WIRE RESISTANCE RATIO

BACKGROUND OF THE INVENTION

1. Field of the Invention

The present invention generally relates to a gas sensor using an oxygen-ion conductor, and particularly to a gas sensor having at least one cavity formed in the oxygen ion conductor and an internal electrode formed inside the cavity wall made of the oxygen-ion conductor. More Specifically, the present invention relates to an e.m.f. cell (or rather electromotive force cell) formed in such a sensor that is temperature-controlled by detecting an internal resistance of the e.m.f. cell that is used as an accurate reference oxygen source for detecting a low concentration of a specific gas such as $O_2$, NOx, HC, $H_2$, CO, $CO_2$ and $H_2O$.

2. Description of the Related Art

A gas sensor using an oxygen-ion conductor, having at least one cavity or chamber formed inside the oxygen-ion conductor and a diffusion resistance hole capable of communicating a gas mixture from outside into the cavity is known for measuring an amount or concentration of a specific gas component contained in the gas. For instance, U.S. Pat. No. 5,700,367 to Yamada et al relates to such a sensor having one cavity. Published European Patent Applications (EP 0810430 A2 and EP 0859232 A2) relate to such a gas sensor having two cavities.

When a gas mixture containing a specific gas component such as NOx and oxygen is introduced into a first cavity of the sensor having two cavities, it is understood that oxygen contained in the mixture gas that enters into the first cavity is pumped out through an oxygen-ion pumping cell so that the specific gas that flows from the first cavity to the second cavity can be measured accurately based on a small constant oxygen concentration (offset level) and a variation in the oxygen concentration. This variation is caused by the specific gas component decomposing or burning inside the second cavity. The gas component amount (or concentration) is determined based on the amount of the oxygen produced or decreased by such decomposition or burning and the offset level of the amount of oxygen which enters into the second cavity.

However, in order to precisely or rather accurately determine the specific gas component amount on such a small order, for instance, of less than 500 PPM or less than 100 PPM by the sensor, it is understood that the total amount of oxygen entering into the second cavity other than the oxygen produced or decreased as a result of decomposition or burn of the gas component in the second cavity should be as small as possible. This is because a small amount of the specific gas component can be notably compared with the total amount of the oxygen in the second cavity. In other words, oxygen not entering through the diffusion resistance hole formed between the cavities but rather entering through other portions such as a third cavity or an internal oxygen-reference electrode formed in the third cavity should be minimized.

In addition, the constant oxygen partial pressure detected at the internal oxygen reference electrode or in the internal oxygen reference cavity becomes critical when accurate measurement of the small amount of the specific gas component is required. This is because the oxygen partial pressures in the first cavity and/or the second cavity must be referred or compared with the constant oxygen partial pressure at the internal reference electrode or in the internal-reference cavity. In other words, the e.m.f. voltage that determines the partial oxygen pressure in the first or second cavity is importantly determined based on the Nernst equation by reference to the oxygen partial pressure appearing at the oxygen-reference electrode or in the internal oxygen-reference cavity.

Therefore, the present inventors consider that the measurement accuracy of the specific gas component depends on how good or how precisely such an e.m.f. voltage cell or the cell that determines the oxygen variation in the first and/or second cavity is designed or structured.

SUMMARY OF THE INVENTION

It is therefore an object of the present invention to provide a gas sensor which is capable of accurately measuring a concentration of a specific gas component such as NOx, $O_2$, $CO_2$, SOx, $H_2O$, CO, HC and $H_2$ contained in a gas mixture of interest such as an exhaust gas emitted from an automobile internal combustion engine.

It is another object of the present invention to provide a gas sensor structure which is capable of accurately detecting a temperature of the gas sensor and of effectively controlling the sensor temperature.

There is provided in accordance with a first aspect of the invention., as may be referred in FIGS. 1 and 2, a gas sensor (1) using two oxygen ion conductor substrates (21),(23): comprising, a cavity (5) formed between the oxygen-ion conductors (21),(23);

a diffusion hole (3) formed as an entrance to the cavity (5);

an internal electrode (23a) formed on an internal wall of one of the oxygen-ion conductor (23) and another electrode (23b) formed on the oxygen-ion conductor (23) spaced from the internal electrode (23a), forming an electromotive force cell that detects an oxygen partial pressure in the cavity (5);

a metallic wire (23c) formed along the oxygen ion conductor (22) so as to connect one end of the metallic wire (23c) to the internal electrode (23a);

another metallic wire (23d) formed along the oxygen ion conductor (22) so as to connect one end of the another metallic wire (23d) to the another electrode (23b); and a heater (30) for heating and activating the oxygen-ion conductor (22);

wherein a combined resistance (Rpvs) determined by applying a stepped current between the other end of the metallic wire (23c) and the other end of the another metallic wire (23d) at a high temperature of 500–900° C. that activates the oxygen-ion conductor (22) so as to transfer oxygen ions has a value not less than 2.6 times greater than that of a lead-resistance (Rlead) in total of the two metallic wires (23c),(23d), the lead-resistance (Rlead) being the value measured along the two metallic wires (23c),(23d) excluding a cell internal resistance of the electromotive force cell appearing across the electrodes (23a),(23b), and the combined resistance (Rpvs) including the lead-resistance (Rlead) and the cell internal resistance.

In the sensor according to the invention, an accuracy range of temperature control in the temperature range of 500–900° C. becomes less than 5° C. If the combined resistance is not less than 4 times greater than the lead-resistance, the accuracy range advantageously becomes less than 2.5° C.

A temperature variation lowers to less than 5° C. if the combined resistance is higher than 50 ohms and the lead-resistance is designed to less than ⅓ of the combined resistance. The very low temperature variation is attained when the combined resistance is designed to higher than 80 ohms at 700° C. and the lead-wire resistance is less than ⅕ of the combined resistance. It is important to reduce the total lead wire resistance to be less than ⅓ of the combined resistance (Rpvs) of an e. m. f. cell (or oxygen detection cell) incorporated in the NOx sensor which is further described in the detailed description.

The above sensor (1) may further include a third oxygen-ion conductor (25) spaced from one of the oxygen-ion conductor (23); a second cavity (9) formed between the third oxygen-ion conductor (15) and the oxygen ion conductor (23); a second internal electrode (25a) formed on the third oxygen-ion conductor and inside the second cavity (9); another second electrode (25b) formed on the third oxygen-ion conductor and outside the second cavity (9); and a second diffusion hole (7) formed between the first cavity (1) and the second cavity (9).

In a second aspect of the invention, there is provided, as may be referred in FIG. 9, an improved gas sensor (51) that differs from the sensor (1) previously described, in that the electrodes (23b),(25b) for oxygen-reference in FIG. 9 are placed in a common cavity (53) providing the same internal oxygen-partial pressure to the electrodes (23b),(25b).

This second aspect of the invention is also important in providing a high accuracy measurement sensor, because the first cavity (5) and the second cavity (9) are interrelated through the second diffusion hole (7) and need the same oxygen reference atmosphere that is formed inside the common cavity (53).

The third aspect of the invention relates to a distance of the electrode (23b) for oxygen reference and the metallic wire (23c) away from the second cavity (9). If the distance of the electrode (23b) or the metallic wire (23c) are too close to or less than 0.5 mm away from the cavity (9), leakage of oxygen occurs and causes a offset second current (Ip2 offset) to flow unnecessarily high rendering inaccurate measurement of a specific gas concentration contained in the oxygen-containing gas.

DETAILED DESCRIPTION OF THE INVENTION

Figure 1:
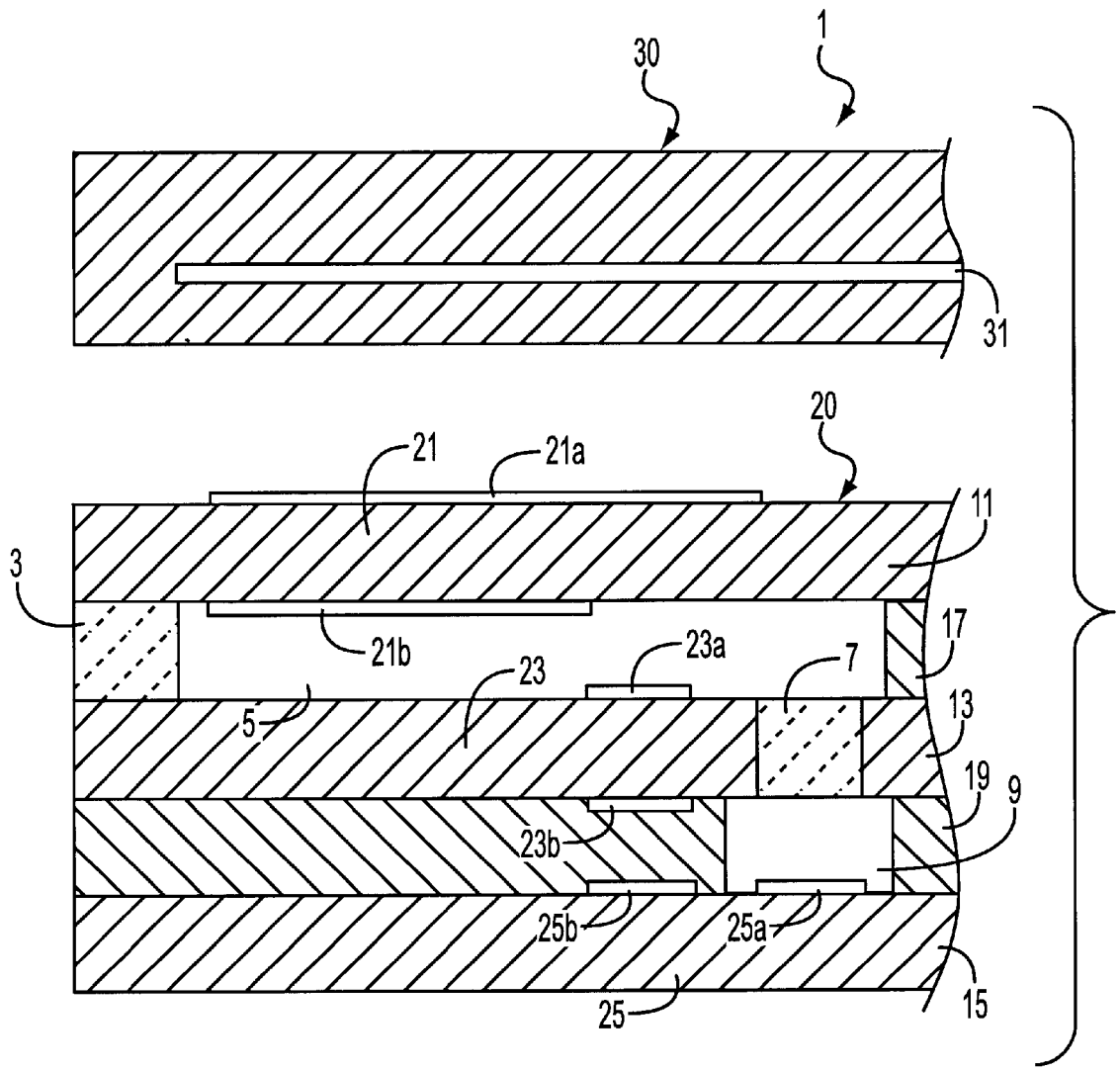
FIG. 1 is a drawing showing a longitudinal cross section of a two-cavity gas sensor (1) to which the present invention is applied.

An embodiment of the present invention will now be described with reference to the drawings. However, the present invention should not be construed as being limited thereto. FIG. 1 schematically shows a longitudinal section of a gas sensor 1 to which the present invention is applied. The gas sensor 1 in this embodiment is a so-called NOx sensor used for measuring the concentration of nitrogen oxide contained in an exhaust gas from, for example, an automobile internal combustion engine. Since the greater part of the nitrogen oxide (NOx) contained in the exhaust gas is nitrogen monoxide (NO), the measurement of NO concentration will be described.

As shown in FIG. 1, the gas sensor 1 is formed by laminating zirconia sheets(or oxygen-ion conductor substrates) 11, 13, 15 and alumina insulating layers 17, 19 so that an exhaust gas as a gas to be measured from an automobile internal combustion engine flows to a second chamber 9 via a first diffusion passage (first diffusion hole) 3, a first chamber (first cavity) 5 and a second diffusion passage (or second diffusion hole) 7 in the mentioned order. A heater base 30 for heating a detecting element body 20, which is formed by laminating these sheets and layers, and activating the same, is provided in a position in the vicinity of the detecting element body 20.

The zirconia sheet 11 disposed most closely to the heater base 30 is provided on both surfaces thereof with porous electrodes 21a, 21b so as to form first oxygen ion pump cell (an oxygen ion pump cell will hereinafter be referred to simply as a pump cell) 21 in the zirconia sheet 11. The zirconia sheet 13 laminated on the zirconia sheet 11 with the first diffusion passage 3, first chamber 5 and alumina insulating layer 17 held therebetween is provided with the second diffusion passage 7, and both surfaces of the portion of the zirconia sheet 13 which is in the vicinity of the second diffusion passage 7 with porous electrodes 23a, 23b so as to form oxygen concentration measuring cell 23. The zirconia sheet 15 laminated on the zirconia sheet 13 with the alumina insulating layer 19 and second chamber 9 held therebetween is provided on the surfaces thereof which are opposed to the second chamber 9 and alumina insulating layer 19 with porous electrodes 25a, 25b so as to form second pump cell 25. The first and second diffusion passages 3, 7 mean portions having diffusion resistance. The heater base 30 contains a heater pattern 31 of platinum therein, and is formed of a base of a ceramic material sintered by using alumina.

This embodiment is formed so that a predetermined very low level of electric current is made to flow between the two porous electrodes 23a, 23b of the oxygen concentration measuring cell 23 with oxygen pumped out on the side of the porous electrode 23b, whereby reference oxygen chambers are formed around the porous electrode 23b, the resultant electrode being used as a self-generation reference electrode. The advantage of forming such a self-generation reference electrode resides in that an oxygen concentration constituting a reference is rarely influenced by the variation of oxygen concentration in the atmosphere.

The second diffusion passage 7 is provided away from the first diffusion passage 3. Providing the second diffusion passage in this manner enables the oxygen concentration in the gas to be measured being introduced into the second chamber 9 to be controlled accurately, so that the dependency of an offset component of a second pump current (electric current flowing in the second pump cell 25) upon the oxygen concentration and the dependency of a dissociation rate of NO upon the oxygen concentration can be reduced. The porous electrode 21b on the portion of the first pump cell 21 which is on the side of the first chamber 5 is short with respect to the length of the first chamber 5 in the longitudinal direction thereof, and formed so as not to extend over the surface of the zirconia sheet 11 which is opposed to the second diffusion passage 7. Forming the porous electrode 21b in this manner enables the influence of the operation of the first pump cells 21 to be reduces to as great an extent as possible, and the oxygen concentration of the gas to be measured flowing into the second chamber 9 to be controlled more accurately.

The porous electrodes 21a–25b are formed with lead wires 23c, 23d (FIG. 2), etc., which will be described below, by the thick film printing of a material containing a metal, such as platinum, palladium, rhodium, gold, silver, copper, etc. as a main component as well as a component identical with that of the zirconia sheets 11–15. The porous electrodes 21a–25b are wired by extending the respective zirconia sheets 11–15 in the rightward direction of FIG. 1, and terminals to be connected to a measuring circuit are provided on the other portions of these zirconia sheets and electrically connected thereto.

Figure 2A:
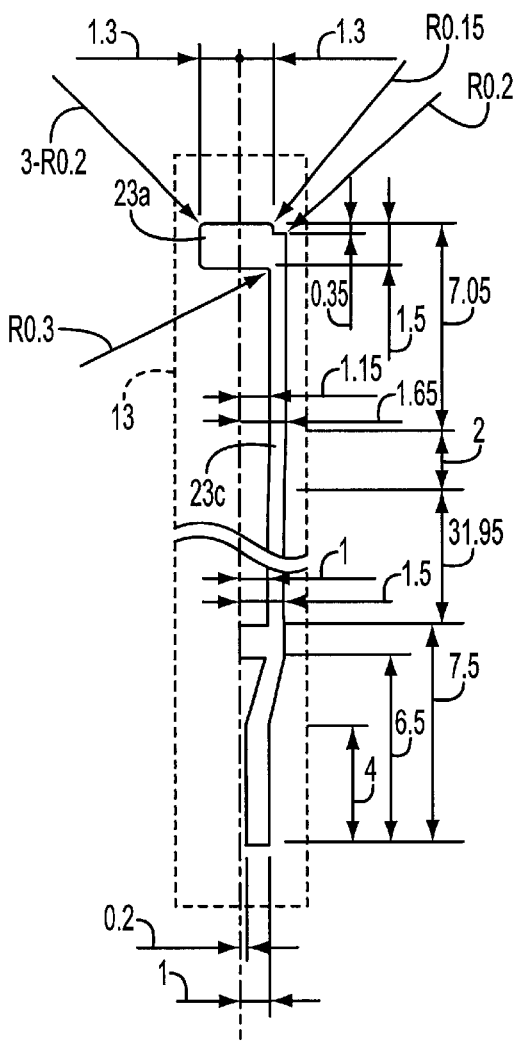
FIG. 2(a) is a drawing showing a shape of an internal porous electrode (23a) formed on an internal wall of an oxygen ion conductor plate (23) in FIG. 1 and a metallic lead wire (23c) connected to the internal electrode (23a) in FIG. 1, forming an electromotive force cell electrode inside a first cavity (5) formed in the gas sensor as shown in FIG. 1.
Figure 2B:
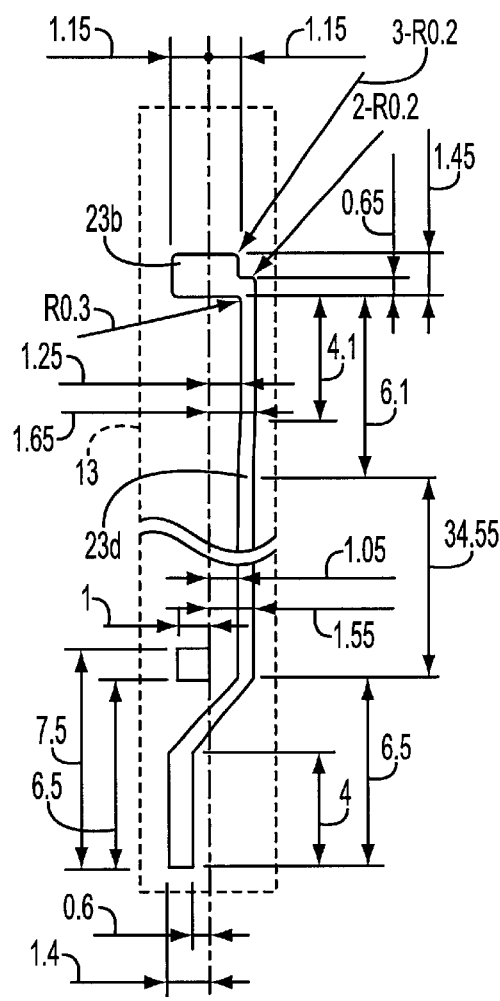
FIG. 2(b) is a drawing showing a shape of an oxygen reference electrode (23b) and a metallic lead wire (23d) connected to the oxygen reference electrode in FIG. 1 or FIG. 9.

FIG. 2(A) shows the shapes of the porous electrode 23a and the lead wire 23c thereof viewed from the upper side of the zirconia sheet 13, and FIG. 2(B) the shapes of the porous electrode 23b and the lead wire 23d thereof viewed from the underside of the zirconia sheet 13. The unit of the sizes shown on FIGS. 2(A) and 2(B) is in millimeters. This mode of embodiment is designed so that the sum Rlead (electric resistance value component of the lead wires) of the resistance values of the lead wires 23c, 23d becomes about 19Ω by forming the lead wires 23c, 23d in this manner.

The internal resistance of the portion of the zirconia sheet 13 which forms the oxygen concentration measuring cell 23 varies in accordance with an element temperature, so that it is possible in this gas sensor 1 to detect the internal resistance on the basis of a resistance value Rpvs (total or combined resistance value) between both ends of the lead wires 23c, 23d, and, furthermore, measure the gas sensor element temperature. Since Rlead of the lead wires 23c, 23d is thus set to a sufficiently low level in this gas sensor, a measurement error of the element temperature can be reduced sufficiently as will be described below. Moreover, as shown in FIGS. 2(A) and 2(B), the lead wires 23c, 23d are provided in the positions which are not directly opposed to each other with the zirconia sheet 13 held therebetween. Accordingly, an electric current flows directly between the lead wires 23c, 23d with the zirconia sheet 13 held therebetween, and the influence upon the resistance Rpvs can be prevented.

The basic operation of this gas sensor 1 will now be described with reference to FIG. 1. In the gas sensor 1, the oxygen concentration (oxygen gas concentration) in the gas to be measured which is being introduced from the first chamber 5 into the second chamber 9 is monitored in the oxygen concentration measuring cell 23. The nitrogen monoxide (NO) and oxygen gas ($O_2$) in the first chamber 5 are dissociated as shown in the following formulae (2), (3), by applying a pump voltage V1 to the first pump cell 21 so that an output voltage Vsm of the oxygen concentration measuring cell 23 comes close to a target voltage (for example, Vs—450 mV) with the oxygen in the first chamber 5 pumped out thereof or pumped thereinto.

$$2NO \rightarrow N_2 + O_2 \qquad (2)$$

$$O_2 + 4e^- \rightarrow 2O^{2-} \qquad (3)$$

Namely, the oxygen concentration in a portion in the vicinity of a gas inflow port of the second chamber 9 is controlled by controlling the operation of the first pump cell 21 so that NO is partially dissociated in the first chamber 5, i.e., so that a dissociation rate a of NO in the gas to be measured in the first chamber 5 becomes not lower than 0.5% (for example, in the range of 2–20%), whereby NO and $O_2$ are dissociated. The electric current (first pump current) Ip1 flowing to the first pump cell 21 at this time is measured.

The gas to be measured from which NO has thus been dissociated at a predetermined dissociation ratio α is sent from the second diffusion passage 7 to the second chamber 9, and the remaining $O_2$ and NO in the gas to be measured are dissociated in the second pump cell 25, the oxygen ions occurring due to the dissociation being pumped out by the second pump cell 25. During this time, the current (second pump current) Ip2 flowing to the second pump cell 25 is measured.

The oxygen ions pumped out at this time are oxygen ions formed by dissociating $O_2$ and NO from the gas to be measured introduced from the first chamber 5 into the second chamber 9. Therefore, the quantity of $O_2$ introduced from the first chamber 5 into the second chamber 9 appears as an offset component (second pump current Ip2 at the time at which the quantity of NO is zero) of the second pump current Ip2, and the remainder turns into an electric current corresponding to the quantity of NO not dissociated in the first chamber 5 but introduced into the second chamber 9.

The NO concentration is then detected by using both the first and second pump currents Ip1, Ip2 thus measured and by a method which will be described later.

The following formula (4) used for detecting NO concentration in the gas to be measured will now be described.

$$\text{NO concentration} = (Ip2 - Ip2\text{offset}) \times A/(1-\alpha/100) \qquad (4)$$

wherein α is a dissociation ratio (%) of NO in the first chamber 5, A is a coefficient for converting a current signal corresponding to the NO concentration into a NO concentration, Ip2 is a current in the second pump cell 25, Ip2offset is an offset component in the current in the second pump cell 25, and NO concentration is the NO concentration of the gas to be measured.

In this mode of embodiment, the first pump cell 21 is controlled so that the output voltage Vsm of the oxygen concentration measuring cell 23 attains a target voltage Vs (for example, 450 mV), and the first pump current Ip1 at this time is measured. Namely, a voltage is applied between the porous electrodes 21a, 21b of the first pump cell 21 so that the oxygen concentration at which NO is dissociated at a predetermined dissociation rate α in the first chamber 5 is attained. During this time, the first pump current Ip1 comes to have a value corresponding to the dissociation rate α of NO in the first chamber 5.

Since the residual NO and $O_2$ not dissociated in the first chamber 5 but flowing into the second chamber 9 are dissociated on the porous electrode 25a of the second pump cell 25, the second pump current Ip2 comes to have a value corresponding to the quantity of oxygen ions occurring due to the dissociation of NO and $O_2$ in the second chamber 9. Namely, the second pump current Ip2 contains not only a current corresponding to the NO concentration but also an offset current corresponding to the oxygen concentration. Therefore, the current corresponding to only the NO concentration in the second chamber 9 is expressed by a difference (Ip2−Ip2offset) between the second pump current Ip2 and offset current Ip2offset).

Let 1 equal the NO concentration in the gas to be measured. The concentration of NO flowing into the second chamber 9 is then (1−α/100), so that a quotient {(Ip2−Ip2offset)/(1−α/100)} obtained by dividing a current difference (Ip2−Ip2offset) by the concentration of NO flowing into the second chamber 9 represents a current value corresponding to a total NO concentration.

Accordingly, the total NO concentration can be determined by multiplying this current value by a predetermined conversion coefficient (coefficient for converting a current value into a NO concentration) A. Namely, the NO concentration can be determined by using the above-mentioned formula (4).

The procedure of measuring NO concentration in a gas to be measured by using the above-described gas sensor 1 and the above-mentioned formula (4) will now be described in order.

Figure 3:
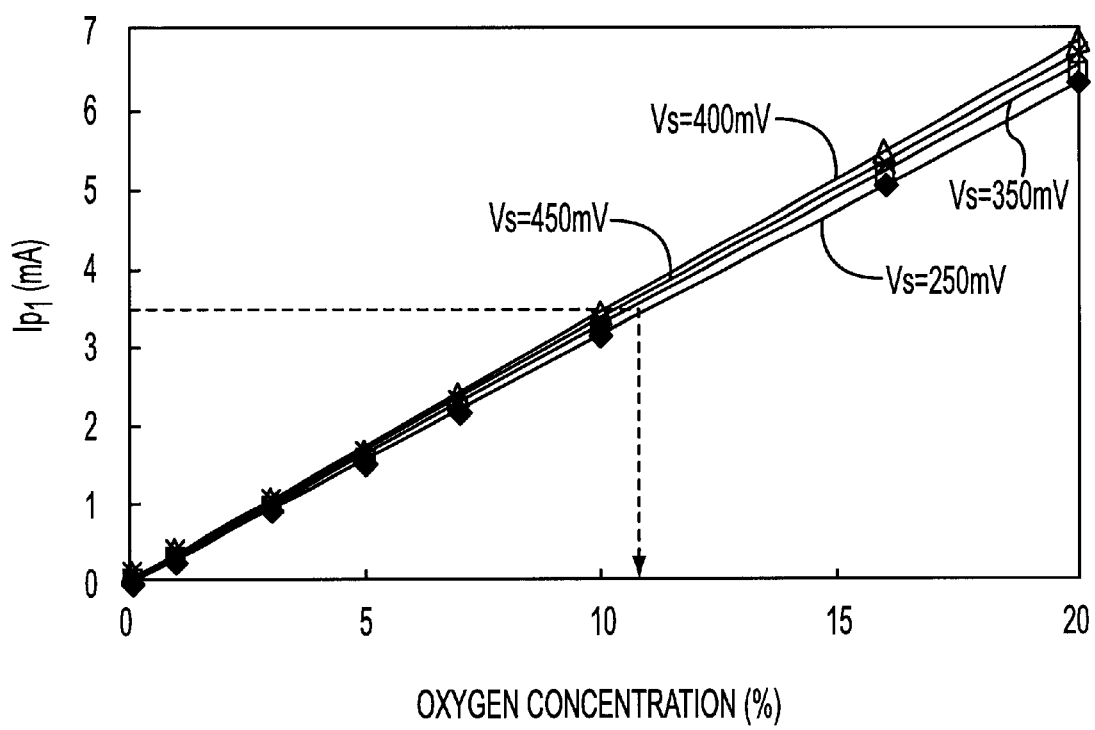
FIG. 3 is a graph showing the relationship between a target voltage of the oxygen concentration measuring cell (that is an electromotive force cell), the first pump current and oxygen concentration.

(1) The relationship between a first pump current Ip1 and an oxygen concentration ($O_2$ concentration) in a gas to be measured is determined in advance by experiment as, for example, in a map M1 shown in FIG. 3, by using as a parameter a set voltage (target voltage) Vs of the oxygen concentration measuring cell 23.

Concretely speaking, the above relation is determined by using a gas to be measured containing $O_2$ alone, so as to eliminate the influence of NO.

Figure 4:
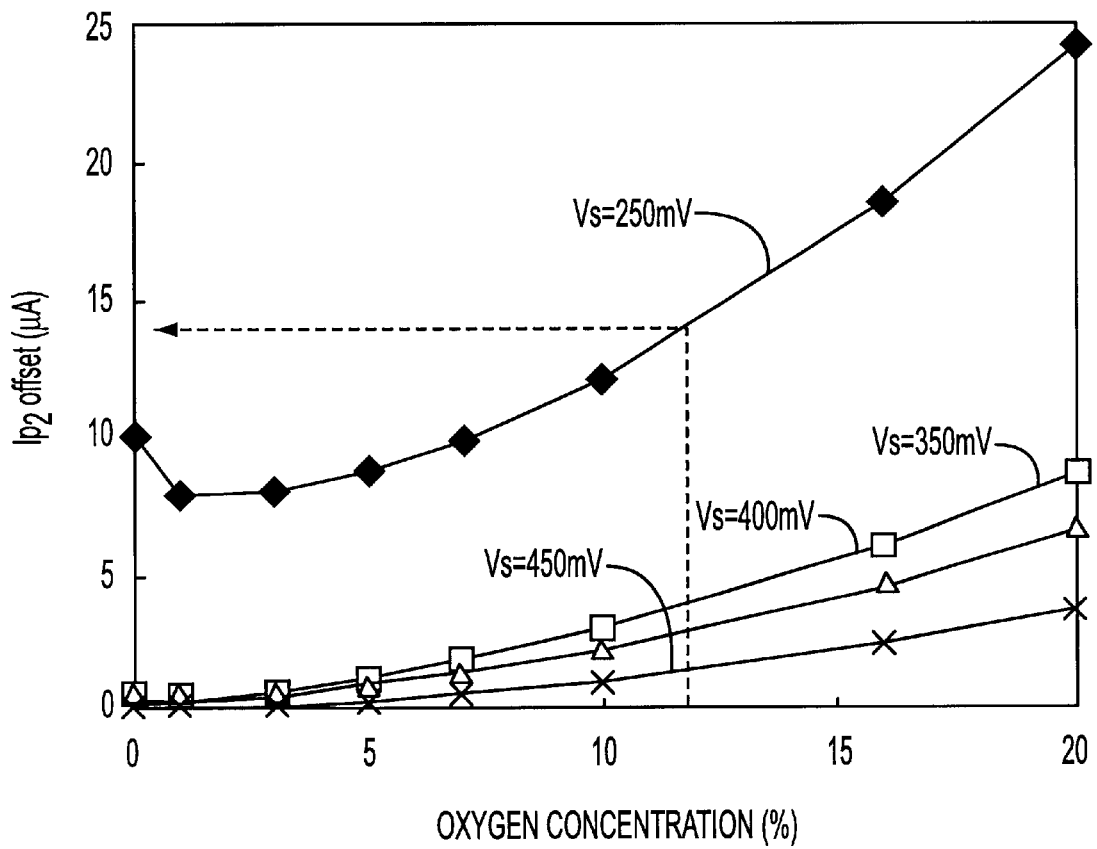
FIG. 4 is a graph showing the relationship between a target voltage of the oxygen concentration measuring cell, offset current and oxygen concentration.

(2) Similarly, the relationship between an offset current Ip2offset and an oxygen concentration ($O_2$ concentration) in a gas to be measured is determined in advance by experiment as in, for example, a map M2 shown in FIG. 4, by using as a parameter a set voltage (target voltage) Vs of the oxygen concentration measuring cell 23.

Concretely speaking, the above relationship is determined by using a gas to be measured containing $O_2$ alone, so as to eliminate the influence of NO. Namely, when the second pump current Ip2 is measured in this stage, the result represents an offset current Ip2offset.

Figure 5:
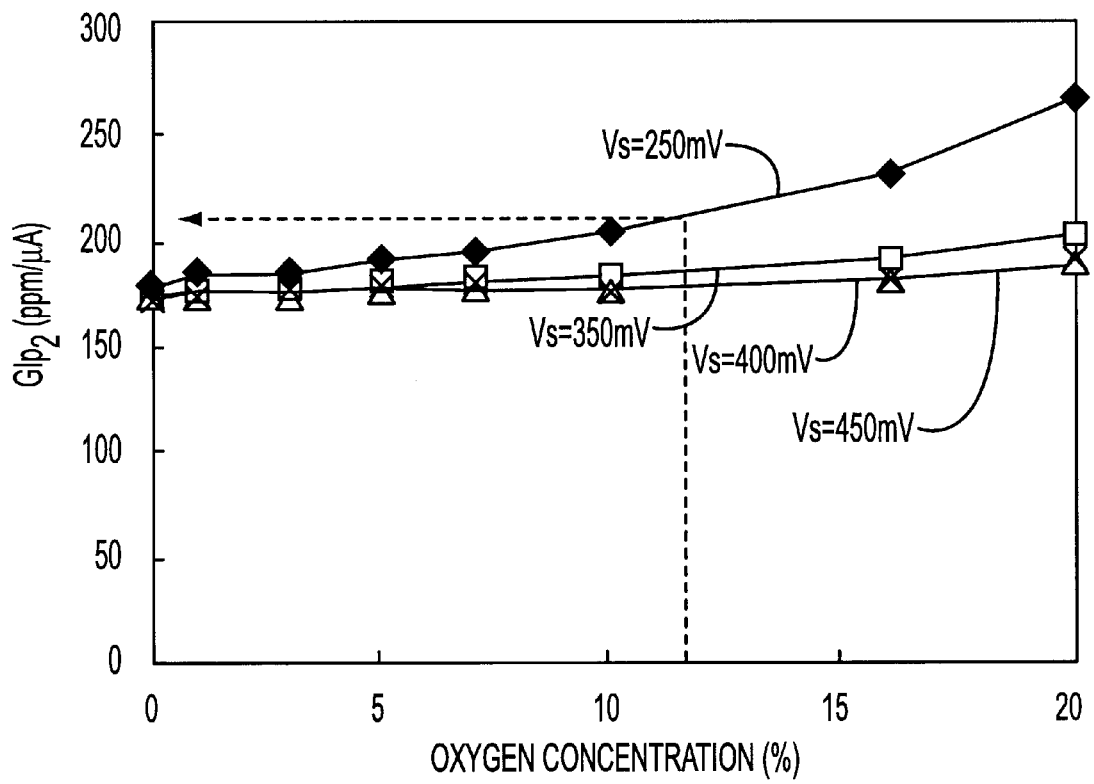
FIG. 5 is a graph showing the relationship between a target voltage of the oxygen concentration measuring cell, gain and oxygen concentration.

(3) The relationship between gain (GIp2) and an oxygen concentration ($O_2$ concentration) in a gas to be measured is determined in advance by experiment as in, for example, a map M3 shown in FIG. 5, by using as a parameter a set voltage (target voltage) Vs of the oxygen concentration measuring cell 23.

This gain is a multiplier used for the detection of the NO concentration, and a function of the target voltage Vs and oxygen concentration to be experimentally determined.

Namely, the gain is a value obtained on the basis of a conversion coefficient (coefficient for converting a current into a NO concentration) A in the condition in which a NO dissociation rate is 0% with a NO dissociation rate α taken into consideration, and represents the variation of the NO concentration corresponding to that of a predetermined current value.

The gain is an inverse of sensitivity represented by a value (for example, a value of a unit of $\mu A/ppm$) obtained by dividing a current corresponding to NO by a NO concentration.

Concretely speaking, the above relationship is determined as follows.

Figure 7:
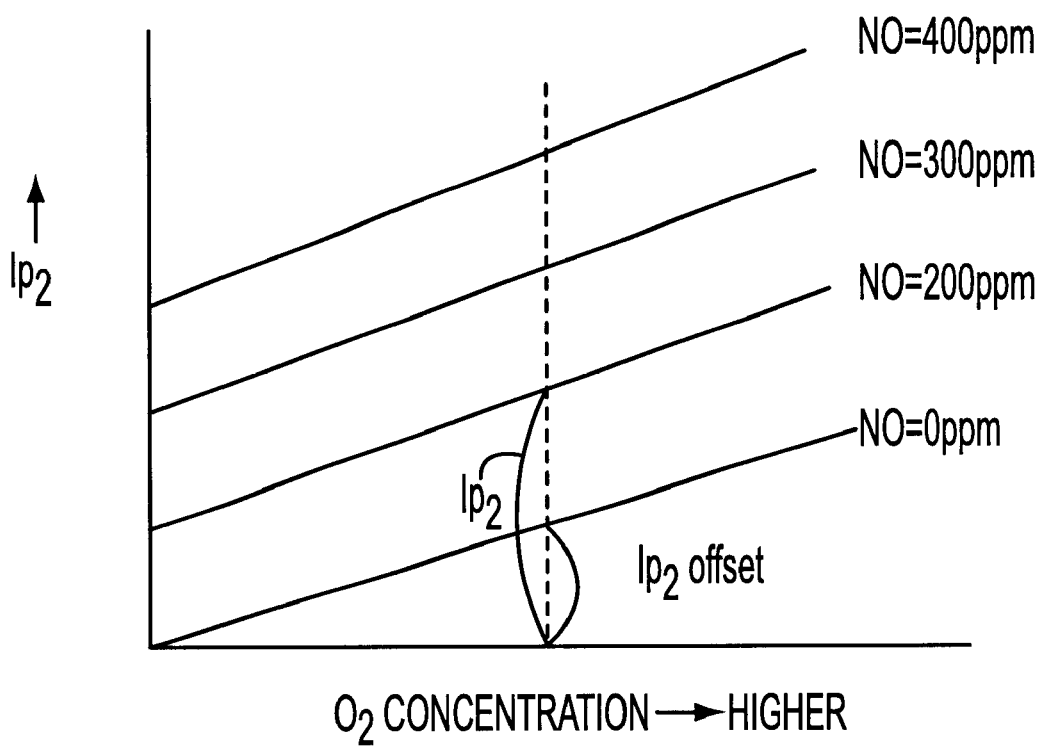
FIG. 7 is a graph showing the relationship between NO concentration, the second pump current and oxygen concentration.

When a known gas to be measured is used, the relationship shown in FIG. 7 is obtained between a second pump current Ip2, an oxygen concentration and NO concentration. Therefore, on the basis of FIG. 7, a current difference (Ip2−Ip2offset) at a certain oxygen concentration with a NO concentration at a certain level (for example, 200 ppm) represents a current value really corresponding to the NO concentration. Therefore, when the current difference (for example, (Ip2−Ip2offset) $\mu A$) is divided by the actual NO concentration (for example, 200 ppm), the sensitivity is determined, and an inverse thereof represents gain GIp2. Accordingly, the map 3 indicating the relationship between gain GIp2, a target voltage Vs and an oxygen concentration as shown in FIG. 5 is prepared by using the gain thus obtained.

(4) A method of measuring actual NO concentration carried out by using the above-mentioned maps M1–M3 will now be described.

First, the gas sensor 1 is placed in an atmosphere of a gas to be measured of unknown NO concentration, and the gas to be measured is introduced into the first chamber 5 via the first diffusion passage 3.

The gas to be measured introduced into the first chamber 5 is subjected to the dissociation of NO and $O_2$ so that a predetermined dissociation rate α (not smaller than 0.5%) of NO is attained, by operation of the first pump cell 21 which attains a target voltage Vs in the oxygen concentration measuring cell 23 as mentioned above, and a first pump current Ip1 corresponding to an amount of dissociation flows. First, the first pump current Ip1 at this time is measured.

The gas to be measured which flows from the first chamber 5 into the second chamber 9 via the second diffusion passage 7 contains $O_2$ and NO which are not dissociated in the first chamber 5 but remain. Therefore, the remaining NO and $O_2$ are dissociated by the above-mentioned operation of the second pump cell 25, and a corresponding second pump current Ip2 flows. The second pump current Ip2 at this time is measured.

The oxygen concentration in the gas to be measured corresponding to the target voltage Vs is then determined with reference to the map M1 of FIG. 3 by using the first pump current Ip1 measured as mentioned above.

The offset current Ip2offset corresponding to the target voltage Vs is then determined with reference to the map M2 of FIG. 5 by using the oxygen concentration obtained from the map M1.

Similarly, gain A/(1−α/100) corresponding to the target voltage Vs is determined with reference to the map M3 of FIG. 5 by using the oxygen concentration obtained from the map M1.

The NO concentration can then be measured by substituting the second pump current Ip2, offset current Ip2offset and gain A/(1−α/100), which are obtained as mentioned above, for the above formula (4).

Figure 6:
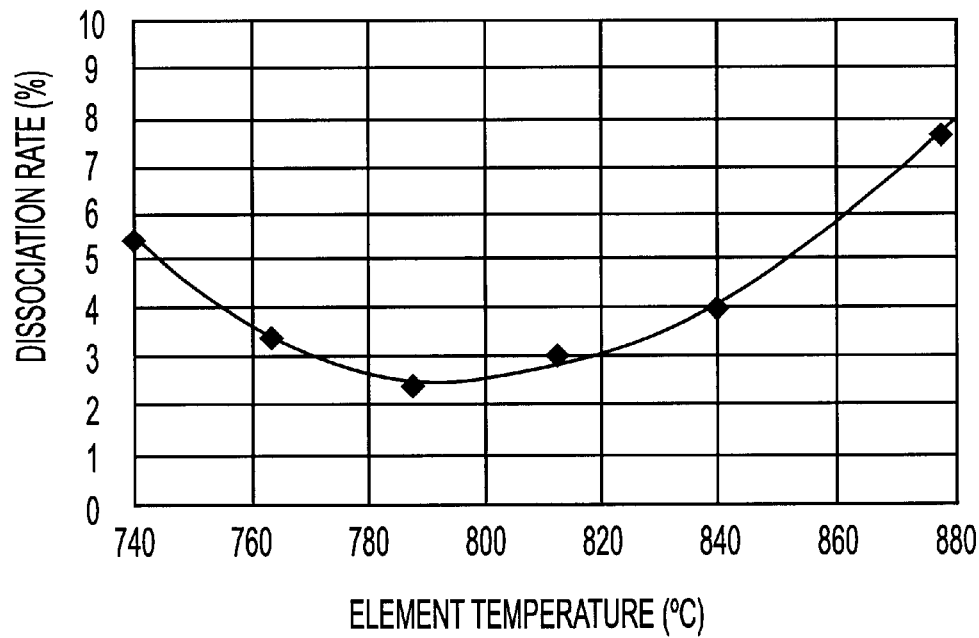
FIG. 6 is a graph showing the relationship between an element temperature and NO dissociation rate in the first chamber.

When the measurement of the NO concentration is thus conducted, it is preferable to control the element temperature to a predetermined level in the range of 550–900° C. by controlling the condition of supplying a current to the heater pattern 31 of the heater base 30. Namely, since the dissociation rate α of NO in the first chamber 5 varies depending upon the element temperature as shown in FIG. 6, it is preferable to use a temperature region in which the dissociation rate α does not greatly vary, for example, a range of 700–850° C., preferably a range of 770–820° C. Therefore, in the gas sensor 1, the element temperature is measured on the basis of the combined resistance value Rpvs between both ends of the lead wires 23c, 23d as mentioned above, and the condition of heating the detecting element body 20 by the heater base 30 is feedback controlled.

Figure 10:
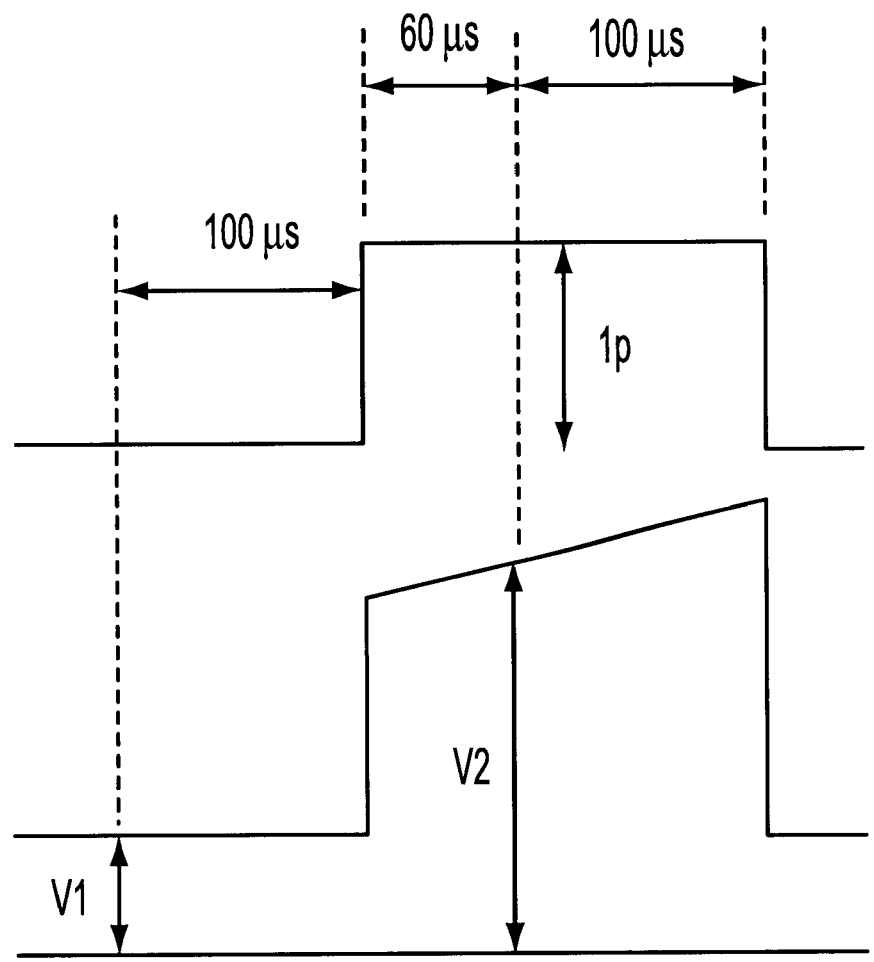
FIG. 10 shows an example method of determining the combined resistance, i.e., a pulse-voltage sensing resistance (Rpvs) that is determined when 60 microseconds has passed after a stepped current is applied across lead wires of an electromotive force cell.

The combined resistance Rpvs is a pulse-voltage sensed resistance measured between the open ends of the metallic lead wires (23c),(23d). In other words, the resistance Rpvs includes the resistance of the oxygen-ion conductor (23) sandwiched by the electrodes (23a),(23b), the resistance of the electrodes (23a),(23b) and the resistance of the metallic wires running through the body (20). The resistance Rpvs is determined, as referred in FIG. 10, by applying a stepped current IP and using the following equation; Rpvs=(V2−V1)/IP, where V2 is the value on 60th microsecond after the stepped current having a direct IP value is applied.

Figure 8:
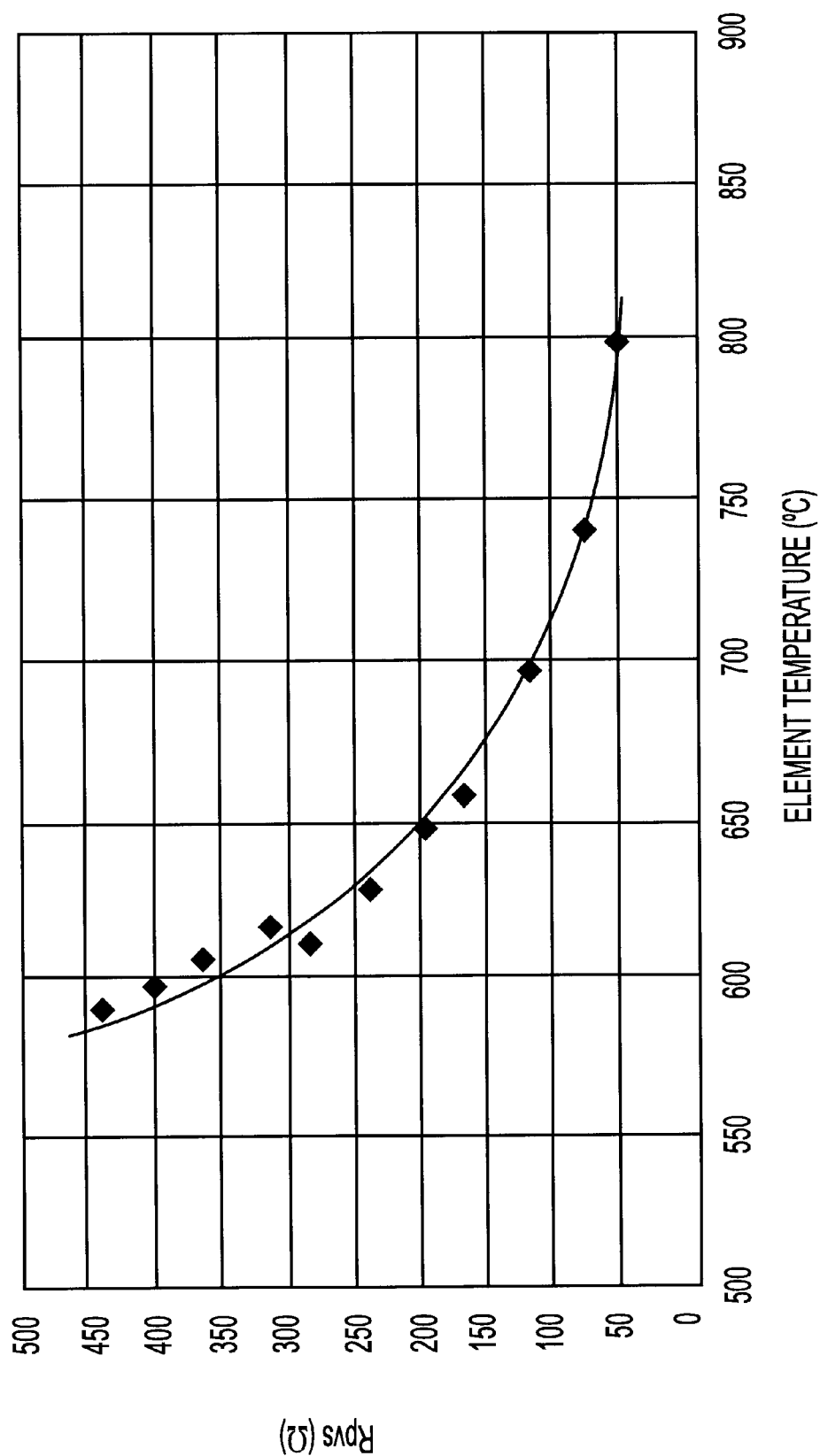
FIG. 8 is a graph showing the relationship between resistance (Rpvs) across the lead wires as a function of sensor temperature.
Figure 9:
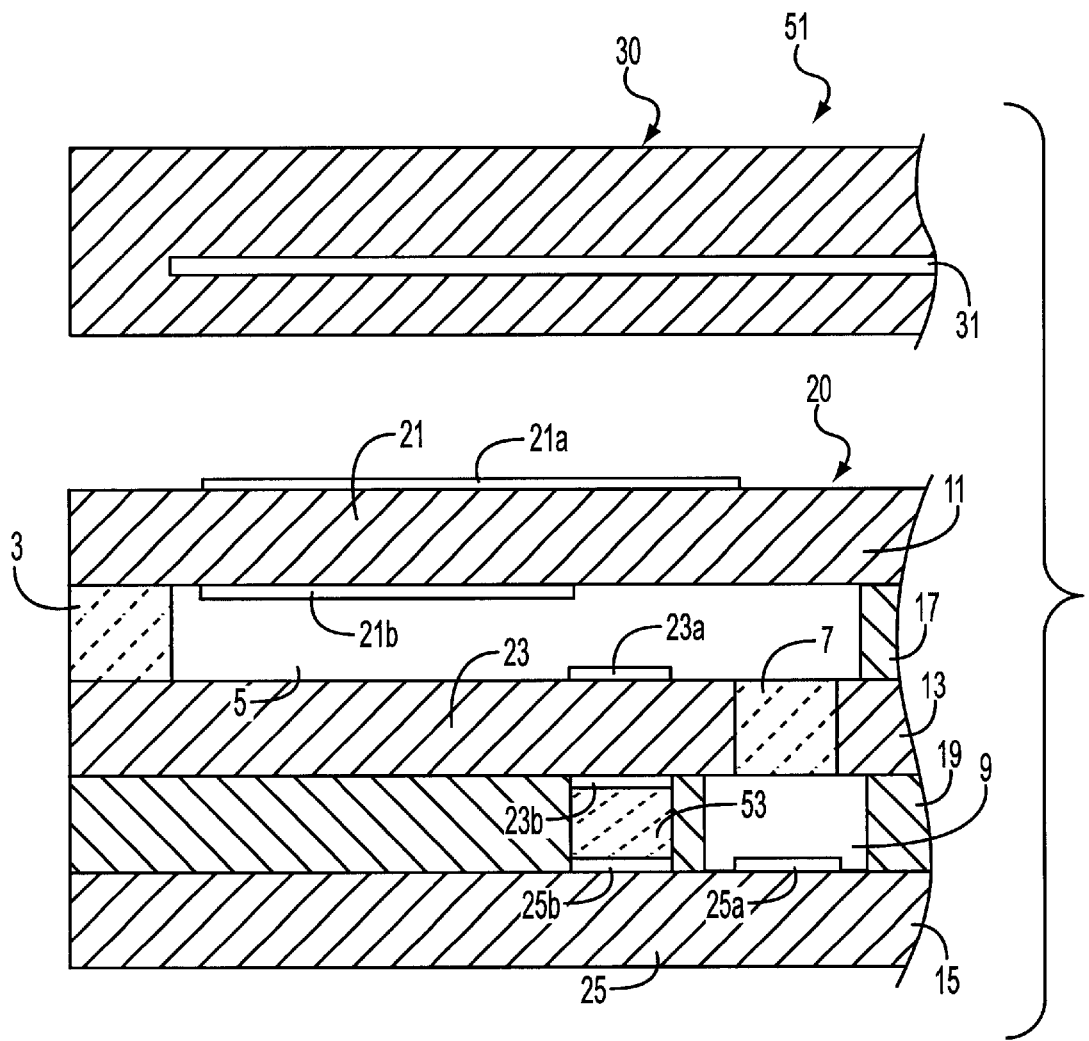
FIG. 9 is a drawing showing a longitudinal cross section of another gas sensor to which the present invention is applied.

Namely, the element temperature and Rpvs has a relationship as shown in FIG. 8. Therefore, in the gas sensor 1, a special mode of measuring Rpvs is interruption executed at intervals of certain seconds, and the condition of supplying a current to the heater pattern 31 is thereby controlled so that the measured Rpvs attains, for example, 80Ω corresponding to an element temperature of 740° C.

In the case where the lead wires 23c, 23d are formed by thick film printing as mentioned above, even if around 10% scatter occurs in the resistance value Rlead of the lead wires 23c, 23d themselves, Rlead is comparatively small as 19Ω as compared with the 80Ω of Rpvs at 740° C. Accordingly, a measurement error of temperature occurring due to the above-mentioned scatter will be small as 1.9° C. or so. This invention teaches that the element temperature can be feedback controlled excellently so that the NOx concentration or oxygen detecting accuracy in the two-cavity sensor is remarkably improved if the Rlead values are made much smaller than the Rpvs value. The Rlead is measured by applying direct current through the metallic lead wires with shortcut of the resistance Rpvs at ambient temperature.

Some noticeable points in the relationship between Rpvs and element temperature shown in FIG. 8 are seen in Table 1. As is clear from Table 1, it is understood that, in a region in the vicinity of Rpvs=80Ω, the corresponding element temperature varies by 1.34° C. every time Rpvs varies by 1Ω (This 1.34° C./Ω will hereinafter be called a temperature resistance coefficient). Therefore, even when Rlead has a scatter of about 1.9Ω(=0.1×Rlead), a measurement error of the element temperature ascribed to the scatter is held to an extremely low level of about 2.5° C., so that the NOx detecting accuracy can be improved greatly as mentioned above, by feedback controlling the cell element temperature excellently.

TABLE 1

| Rpvs (Ω) | Element temperature (° C.) |
|---|---|
| 60 | 772.2 |
| 65 | 763.2 |

TABLE 1-continued

| Rpvs (Ω) | Element temperature (° C.) |
|---|---|
| 70 | 755.0 |
| 72 | 751.9 |
| 75 | 747.4 |
| 80 | 740.5 |
| 85 | 734.0 |
| 88 | 730.4 |
| 90 | 728.0 |
| 95 | 722.4 |
| 100 | 717.2 |

In other words, the variation of a measured temperature value obtained when Rpvs varies 100% comes to about 100° C./100% (this will hereinafter be called a rate of change in resistance temperature) in the estimation based on linear approximation made in the vicinity of the region of Rpvs=80Ω, and a measurement error of the element temperature calculated by multiplying this rate of change in the resistance temperature by 0.1×Rlead/Rpvs is about 2.5° C. Thus, it is understood that the object of controlling the element temperature can be attained satisfactorily. Namely, the gas sensor thus formed satisfies the following expression:

Desired range of temperature measurement error >0.1× Rlead×Rate of change in resistance temperature/Rpvs

EXAMPLE

The present invention is now illustrated by means of the following Example. However, the present invention should not be construed as being limited thereto.

The gas sensor 1 of the above mode of embodiment was manufactured practically, and the effect thereof concerning the temperature measurement error was verified. First, five gas sensors 1 were manufactured, and Rlead of each thereof was measured. The Rlead values of the gas sensors were 19.6Ω, 19.4Ω, 19.0Ω, 18.7Ω, 17.9Ω, and it was ascertained that an average of the Rlead's was 18.9Ω, and that the Rlead's had a scatter of about 10%. Various types of gas sensors 1 having different Rpvs values were manufactured by varying the area of the porous electrodes 23a, 23b or the thickness of the zirconia sheet 13. The characteristics of each gas sensor 1 are shown in Table 2. The internal resistance in Table 2 represents that of the zirconia sheet 13 constituting the oxygen concentration measuring cell.

TABLE 2

| Rpvs (Ω) | Internal resistance (Ω) | Rlead (Ω) | Internal resistance/ Rlead | Rpvs/ Rlead | Temperature resistance coefficient (° C./Ω) | Temperature measuring error (° C.) |
|---|---|---|---|---|---|---|
| 40 | 21.1 | 18.9 | 1.1 | 2.1 | 3.88 | 7.33 |
| 50 | 31.1 | 18.9 | 1.6 | 2.6 | 2.63 | 4.98 |
| 60 | 41.1 | 18.9 | 2.2 | 3.2 | 1.99 | 3.77 |
| 80 | 61.1 | 18.9 | 3.2 | 4.2 | 1.34 | 2.53 |
| 100 | 81.1 | 18.9 | 4.3 | 5.3 | 1.01 | 1.91 |

As understood from Table 2, when Rpvs is set to not smaller than 2.6 times as high as Rlead, the temperature measuring error can be reduced to lower than 5° C. When the gas sensor 1 attains this level of accuracy, most of the High temperature gas sensors will sufficiently serve the purpose. The Rpvs is preferably set not smaller than 4 times as high as Rlead, and, in this case, the temperature measuring error can be held down to as low as around 2.5° C. The NOx sensor that requires a high accuracy measurement need such Rpvs value more than 5 times higher than Rlead.

In the above example, the zirconia sheet 13 constituting the oxygen concentration measuring cell 23 corresponds to the solid electrolytic member, the second chamber 9 the gas chamber, and the second pump cell 25 the oxygen ion pump cell respectively. The present invention is not limited at all to the above-described embodiment, and it can, of course, be practiced in various modes within the range not departing the gist of the invention. For example, in the above mode of embodiment, the temperature is detected by the zirconia sheet 13, porous electrodes 23a, 23b and lead wires 23c, 23d which constitute the oxygen concentration measuring cell 23. The temperature may also be detected by using the zirconia sheet 15 and porous electrodes 25a, 25b which constitute the second pump cell 25, or independent electrodes and lead wires may be provided so that they sandwich one of the zirconia sheets 11–15 for carrying out the detection of the temperature. In the latter case, the temperature can be detected continuously at all times, and an operation for switching the mode to the above-mentioned special mode can be omitted. In the former case, the temperature is detected in the above-mentioned mode of embodiment by utilizing the structure of the second pump cell 25 or oxygen concentration measuring cell 23, so that the construction of the gas sensor 1 can be more simplified.

In the above example, feedback control of the heater base 30 is carried out so that the element temperature attains a desired level. Even when the map showing the corresponding relation between an output from the gas sensor 1 and the NOx concentration is corrected on the basis of the temperature measured as mentioned above, the detecting accuracy can be further improved in the same manner. Although the above example is applied to a NOx sensor, the present invention can also be applied to a gas sensor for detecting various kinds of special components (for example, $O_2$, HC, CO, $CO_2$, $H_2$, etc.) other than NOx in a gas to be measured.

This application is based on Japanese Patent Application No. Hei. 11-95194 filed Apr. 1, 1999 which is incorporated herein by reference in its entirety.

What is claimed is:

1. A gas sensor adapted to detect a specific component in a gas to be measured, comprising:
   a solid electrolyte having an internal resistance which varies with temperature and first and second electrodes provided on opposite sides of said solid electrolyte, and
   a pair of lead wires comprising a metallic film supported by opposing sides of said solid electrolyte and being electrically connected to the solid electrolyte via the first and second electrodes, respectively,
   wherein the lead wires, the first and second electrodes and the solid electrolyte have a total effective resistance measured at the end portions of the lead wires which are not connected to the solid electrolyte that is not smaller than 2.6 times the electric resistance of the lead wires at a temperature of 500–1000° C.

2. The gas sensor as claimed in claim 1, wherein the gas sensor includes:
   a gas chamber into which a gas to be measured is introduced,
   an oxygen ion pump cell for decomposing a specific component in the gas to be measured that is introduced into the gas chamber, and for electrically detecting oxygen ions obtained during the decomposition operation, and
   an oxygen concentration measuring cell comprising said solid electrolyte and first and second electrodes for detecting the oxygen concentration of the gas to be measured that is introduced into the gas chamber.

3. The gas sensor as claimed in claim 1, wherein the gas sensor includes:
   a gas chamber into which the gas to be measured is introduced,
   an oxygen ion pump cell comprising said solid electrolyte and first and second electrodes for decomposing a specific component in the gas to be measured that is introduced into the gas chamber, and for electrically detecting oxygen ions obtained during the decomposition operation, and
   an oxygen concentration measuring cell for detecting the oxygen concentration of the gas to be measured that is introduced into the gas chamber.

4. The gas sensor as claimed in claim 1, wherein the lead wires are not directly opposed to each other across the solid electrolyte.

5. A gas sensor (1) including two oxygen ion conductors (21), (23), comprising:
   a first cavity (5) formed between the oxygen-ion conductors (21), (23);
   a diffusion hole (3) formed as an entrance to the cavity (5);
   a first internal electrode (23a) formed on an internal wall of one of the oxygen-ion conductors (23) and a second electrode (23b) formed on the oxygen-ion conductor (23) spaced from the internal electrode (23a), forming an electromotive force cell that detects an oxygen partial pressure in the cavity (5);
   a first metallic wire (23c) comprising a metallic film formed along the oxygen ion conductor (23) so as to connect one end of the metallic wire (23c) to the internal electrode (23a);
   a second metallic wire (23d) comprising a metallic film formed along the oxygen ion conductor (23) so as to connect one end of the second metallic wire (23d) to the second electrode (23b); and
   a heater (30) for heating and activating the oxygen-ion conductor (22);
   wherein a combined effective resistance (Rpvs) determined by applying a stepped current between the other end of the metallic wire (23c) and the other end of the another metallic wire (23d) at a temperature of 500–1000° C. that activates the oxygen-ion conductor (23) so as to transfer oxygen ions has a value not less than 2.6 times greater than the electric lead-resistance (Rlead) in total of the two metallic wires (23c),(23d), the electric lead-resistance (Rlead) being the value measured along the two metallic wires (23c),(23d) excluding a cell internal resistance of the electromotive force cell including electrodes (23a),(23b), the combined resistance (Rpvs) including the lead-resistance (Rlead) and the cell internal resistance.

6. The gas sensor as claimed in claim 5, wherein the combined effective resistance is higher than 50 ohms and the electric lead-resistance is less than ⅓ of the combined effective resistance at a temperature of 600–800° C.

7. The gas sensor as claimed in claim 5, wherein the electric lead-resistance is less than ⅕ of the combined effective resistance at a temperature of 600–800° C.

8. The gas sensor as claimed in claim 5, further including a third oxygen-ion conductor (25) spaced from one of the oxygen-ion conductor (23); a second cavity (9) formed between the third oxygen-ion conductor (25) and the oxygen ion conductor (23); a second internal electrode (25a) formed on the third oxygen-ion conductor and inside the second cavity (9); another oxygen reference electrode (25b) formed on the third oxygen-ion conductor and outside the second cavity (9); and a second diffusion hole (7) formed between the first cavity (5) and the second cavity (9).

9. The gas sensor as claimed in claim 8, wherein the oxygen reference electrodes (23b),(25b) for oxygen-reference are placed in a common cavity (53) providing the same internal oxygen-partial pressure to the electrodes (23b),(25b).

10. The gas sensor as claimed in claim 8, wherein a distance of the electrode (23b) for oxygen reference is located at least 0.5 mm away from the second cavity (9).

11. The gas sensor as claimed in claim 8, wherein the common cavities are located at least 0.5 mm away from the second cavity (9).

12. The gas sensor as claimed in claim 8, for detecting NOx gas at a temperature of 600–900° C.

13. The gas sensor as claimed in claim 5, for detecting NOx gas at a temperature of 600–900° C.

14. The gas sensor as claimed in claim 5, wherein the metallic wire (23c) and the metallic wire (23d) are not directly opposed to each other across the oxygen ion conductor (23).

* * * * *